(12) United States Patent
Kadhiresan et al.

(10) Patent No.: US 6,761,716 B2
(45) Date of Patent: Jul. 13, 2004

(54) SYSTEM AND METHOD FOR ASSESSING ELECTRODE-TISSUE CONTACT AND LESION QUALITY DURING RF ABLATION BY MEASUREMENT OF CONDUCTION TIME

(75) Inventors: Veerichetty A. Kadhiresan, Temecula, CA (US); Marshall L. Sherman, Cardiff by the Sea, CA (US); Wade A. Bowe, Temecula, CA (US)

(73) Assignee: Cardiac Pacemakers, Inc., St. Paul, MN (US)

(*) Notice: Subject to any disclaimer, the term of this patent is extended or adjusted under 35 U.S.C. 154(b) by 35 days.

(21) Appl. No.: 09/955,551

(22) Filed: Sep. 18, 2001

(65) Prior Publication Data

US 2003/0055420 A1 Mar. 20, 2003

(51) Int. Cl.⁷ .......................... A61B 18/12; A61B 18/14
(52) U.S. Cl. ........................................ 606/34; 606/41
(58) Field of Search ....................................... 606/41, 34

(56) References Cited

U.S. PATENT DOCUMENTS

2002/0143326 A1 * 10/2002 Foley et al. .................. 606/41
2003/0045871 A1 * 3/2003 Jain et al. ..................... 606/41

* cited by examiner

Primary Examiner—Lee Cohen
(74) Attorney, Agent, or Firm—Fulwider Patton Lee & Utecht, LLP (57) ABSTRACT

The efficacy of a lesion produced between a pair of ablation electrodes is assessed by analyzing the time it takes for a pulse of energy to travel from one electrode to the other. During a first time period, a first pulse of energy is applied to a first electrode. The time it takes for the pulse to conduct through the tissue to a second electrode is determined. During a time period subsequent to the first time, a subsequent pulse of energy is applied to the first electrode and the time it takes for the subsequent pulse to conduct through the tissue to the second electrode is determined. Changes in the conduction times are monitored by calculating the difference between consecutive conduction times and comparing the difference to a preset value. If the difference is below the preset value the lesion is considered adequate.

32 Claims, 11 Drawing Sheets

SYSTEM AND METHOD FOR ASSESSING ELECTRODE-TISSUE CONTACT AND LESION QUALITY DURING RF ABLATION BY MEASUREMENT OF CONDUCTION TIME

BACKGROUND OF THE INVENTION

1. Field of the Invention

The invention relates generally to an electrophysiological ("EP") system and method for providing energy to biological tissue within a biological site, and more particularly, to a radio frequency ("RF") ablation system and method for determining the adequacy of contact between the system's ablation electrodes and the tissue and the quality, e.g., depth and continuity, of any lesion resulting from RF ablation based on measurements of conduction time through the biological tissue.

2. Description of the Related Art

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed percutaneously, a procedure in which a catheter is introduced into the patient through an artery or vein and directed to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves the formation of continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system providing RF ablation therapy. In this therapy, transmural ablation lesions are formed in the atria to prevent atrial reentry and to allow sinus impulses to activate the entire myocardium. In this sense transmural is meant to include lesions that pass through the atrial wall from the interior surface (endocardium) to the exterior surface (epicardium).

During ablation, to obtain a transmural lesion, it is necessary to places the electrodes on the catheter in intimate contact with the target tissue. Initial positioning of the electrodes within the atria and placement against the endocardium is typically done visually under fluoroscopy imaging. RF energy is applied to the electrodes to raise the temperature of the target tissue to a non-viable state. In general, the temperature boundary between viable and non-viable tissue is approximately 48° Centigrade. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C. In clinical applications, the target temperature is set below 70° C. to avoid coagulum formation. Coagulum formation can also be avoided by monitoring electrode impedance which is the ratio of voltage over current. A rise in electrode impedance during ablation would indicate coagulative adhesion of tissue components or tissue charring at the electrode tissue interface.

Once ablation therapy is completed, pre-ablation and post-ablation electrocardiograms (ECG) may be compared to assess lesion quality. However, because ECG amplitudes may not be highly sensitive or specific to lesion formation the accuracy of lesion quality assessment in this manner is questionable. Lesion quality assessment in this manner is also inconvenient in that it requires the use of additional ECG instrumentation.

Hence, those skilled in the art have recognized a need for an RF ablation system and method for assessing the adequacy of the contact between biological tissue and ablation electrodes and for assessing the adequacy of a lesion resulting from the application of RF energy through the electrodes. The need for providing such assessments without reliance on electrocardiogram measurements has also been recognized. The invention fulfills these needs and others.

SUMMARY OF THE INVENTION

Briefly, and in general terms, the invention is directed to methods and systems for assessing the adequacy of a lesion resulting from the application of RF energy through the electrodes and for assessing the adequacy of the contact between biological tissue and ablation electrodes.

In a first aspect, the invention relates to a method of assessing the efficacy of a biological tissue lesion between a pair of the electrodes in an ablation procedure using a catheter system having a catheter with a plurality of electrodes and a generator for providing energy to the electrodes. During a first time period, a first pulse of energy is applied to a first electrode. A first conduction time based on the time it takes for the pulse to conduct through the tissue to a second electrode is determined. During a time period subsequent to the first time, a subsequent pulse of energy is applied to the first electrode and a subsequent conduction time is determined based on the time it takes for the subsequent pulse to conduct through the tissue to the second electrode. Changes in the conduction times are monitored to assess lesion efficacy.

In another aspect, the invention relates to a system for assessing the efficacy of a biological tissue lesion between a first electrode and a second electrode positioned proximal to the biological tissue. The system includes a generator adapted to output a pulse of energy and a processor adapted to control the generator such that an energy pulse is provided to the first electrode at a first pulse-application time. The processor monitors electrical activity at the second electrode for an indication that the energy pulse has been sensed by the second electrode and records the time at which the pulse was sensed. The processor further determines a conduction time based on the difference between the pulse-application time and the pulse-sense time. The processor repeats the conduction time measurement at least once, at a time subsequent to the first pulse application time, and monitors changes in the conduction times to assess lesion efficacy.

In another aspect, the invention relates to a method of assessing the efficacy of a biological tissue lesion between pairs of electrodes in an ablation procedure using a catheter system having a catheter with a plurality of electrodes and a generator for providing a sequence of energy pulses to the electrodes. During a first time period, an initial sequence of energy pulses is applied to the plurality of electrodes such that a first pulse is applied to a first electrode, a second pulse is applied to a second electrode and so on. For each pulse, the time it takes for the pulse to conduct through the tissue to at least one of the other electrodes is determined. During a time period subsequent to the first time period, a subsequent sequence of energy pulses is applied to the plurality of electrodes in a manner similar to the initial sequence. For each pulse, the time it takes for the pulse to conduct through the tissue to at least one of the other electrodes is determined. For a selected pair of electrodes, changes in the conduction times are monitored to assess lesion efficacy.

In another aspect, the invention relates to a method of assessing the efficacy of a biological tissue lesion using a catheter system having a catheter with at least three electrodes and a generator for providing energy to the electrodes. The method includes positioning the catheter such that two electrodes spaced a distance apart are on opposite sides of the lesion and two electrodes spaced substantially the same distance apart have nonablated tissue there between. The method also includes determining the time it takes for a pulse of energy to conduct between the two electrodes on opposite sides of the lesion and determining the time it takes for a pulse of energy to conduct between the two electrodes having nonablated tissue there between. Further included in the method are calculating a difference between the conduction times and comparing the difference to a preset value. If the difference is below the preset value an indication of an adequate lesion is provided.

In another aspect, the invention relates to a method of assessing contact between the plurality of electrodes and the tissue in an ablation procedure using a catheter system having a catheter with a plurality of electrodes and a generator for providing energy to the electrodes. The method includes positioning the catheter adjacent the biological tissue such that at least one of the electrodes contacts the tissue, applying a pulse of energy to the one electrode in contact with the tissue and monitoring the electrical activity at each of the remaining electrodes for receipt of the pulse.

These and other aspects and advantages of the invention will become apparent from the following detailed description and the accompanying drawings which illustrate by way of example the features of the invention.

BRIEF DESCRIPTION OF THE DRAWINGS

in FIG. 5d, the lesion is transmural and the depth-wise conduction path is blocked;

in FIG. 8c, the lesion is transmural and the depth-wise conduction path is blocked;

DETAILED DESCRIPTION OF PREFERRED EMBODIMENTS

Figure 1:
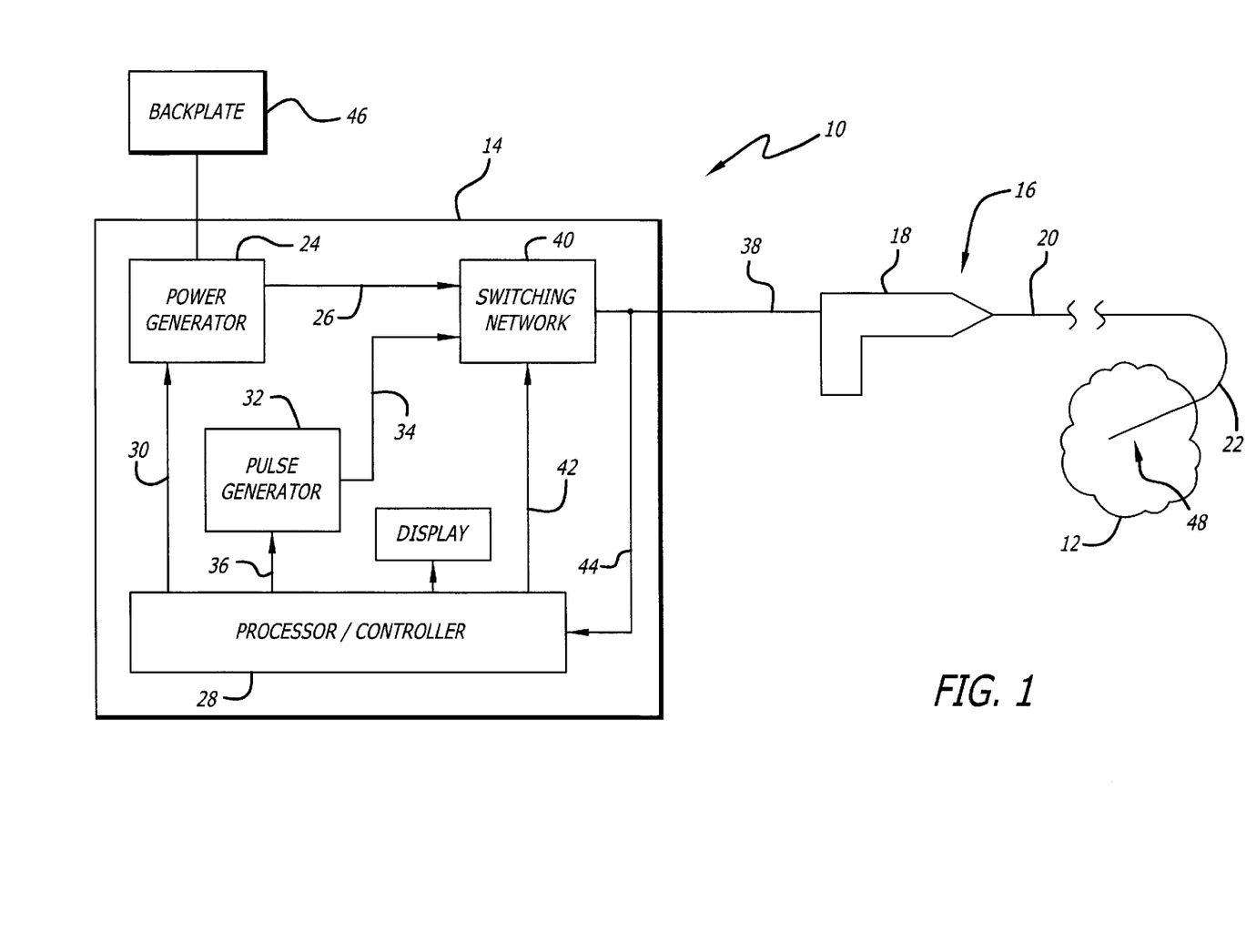
FIG. 1 is a schematic block diagram of an ablation system configured in accordance with aspects of the invention including a power control system ("PCS") and a catheter system.

Turning now to the drawings, in which like reference numerals are used to designate like or corresponding elements among the several figures, in FIG. 1 there is shown a system 10 for use in ablation therapy of a biological site 12, e.g., the atrium or ventricle of the heart. The system 10 includes a power control system 14 and a catheter system 16. The catheter system 16 includes a handle 18 and a steerable catheter sheath 20 having a distal segment 22. The distal segment 22 carries an electrode system 48 and is capable of being percutaneously introduced into the biological site 12.

The power control system 14 includes a power generator 24, that may have any number of output channels through which it provides power or drive 26. The operation of the power generator 24 is controlled by a processor/controller 28 which outputs power control signals 30 to the power generator 24. The power control system 14 also includes a pulse generator 32, that may have any number of output channels through which it provides one or more energy pulses 34. The operation of the power generator 24 is also controlled by a processor/controller 28 which outputs pulse control signals 36 to the pulse generator 32. Power 26 and pulses 34 are output to the catheter system 16 over lead lines 38 through a switching network 40. Operation of the switching network 40 is controlled by switch control signals 42 from the controller 28. The processor 28 monitors the signals present on the lead lines 38 along a monitor line 44.

As described in detail below, the processor/controller 28 controls the switching network 40 such that during certain periods of time, power 26 is applied to one or more electrodes in the electrode system at the distal segment 22 in order to ablate tissue at the biological site and, during other periods of time, one or more pulses are applied to one or more of the electrodes in order to assess the efficacy of the lesion resulting from the ablation. During ablation periods the power 26 is monitored by the processor 28 over the monitor line 44. Based on the power 26 the controller 28 adjusts the operation of the power generator 24. During lesion-assessment periods, pulse signals sensed by the electrodes are monitored by the processor 28 over the monitor line 44. Using these sensed signals the processor 28 determines the time it takes for the applied pulse to propagate through the tissue to the other electrodes. This measure of time is referred to herein as "conduction time." Based on a series of conduction time measurements over a period of time, the processor 28 provides an indication of the efficacy of the ablation lesion and may adjust the power 26 accordingly.

The system 10 may further include a backplate 46. The backplate 46 is connected to the power generator 24 and generally provides a return path for the power 26 delivered to the biological site 12 through the catheter system 16.

Figures 2, 3A:
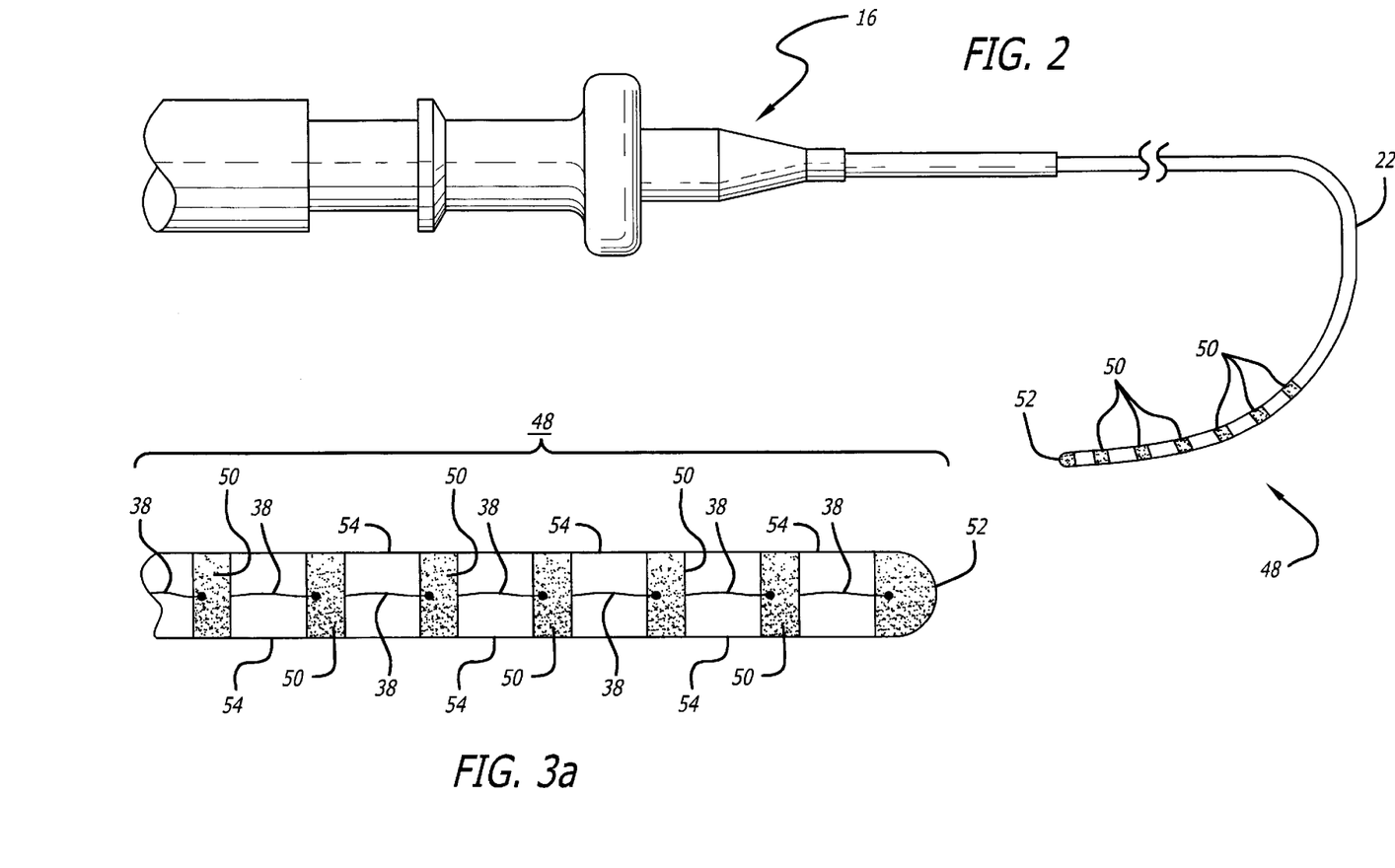
FIG. 2 is a diagram of the catheter system of FIG. 1 presenting more detail that includes a handle and a catheter sheath having a preformed distal segment carrying an electrode system.
FIG. 3a is a detailed schematic block diagram of one configuration of the electrode system of FIG. 2 having a tip electrode and several band electrodes arranged in a linear array.

As shown in FIGS. 2 and 3a, the distal segment 22 of the catheter system 16 includes an electrode system 48 (FIG. 3a). The electrode system 48 is shown in schematic form with the components drawn in more detail to more clearly illustrate the relationship between the components. A preferred embodiment of the electrode system 48 includes six band electrodes 50 arranged in a substantially linear array along the distal segment 22 of the catheter sheath 20. In another embodiment, there are twelve electrodes in the electrode system. The electrode system 48 may include a tip electrode 52. The band electrodes 50 are arranged so that there is space 54 of non-conductive material between adjacent electrodes. In one configuration of the electrode system 48, the width of the band electrodes 50 is 3 mm and the space 54 between the electrodes is 4 mm.

Figure 3B:
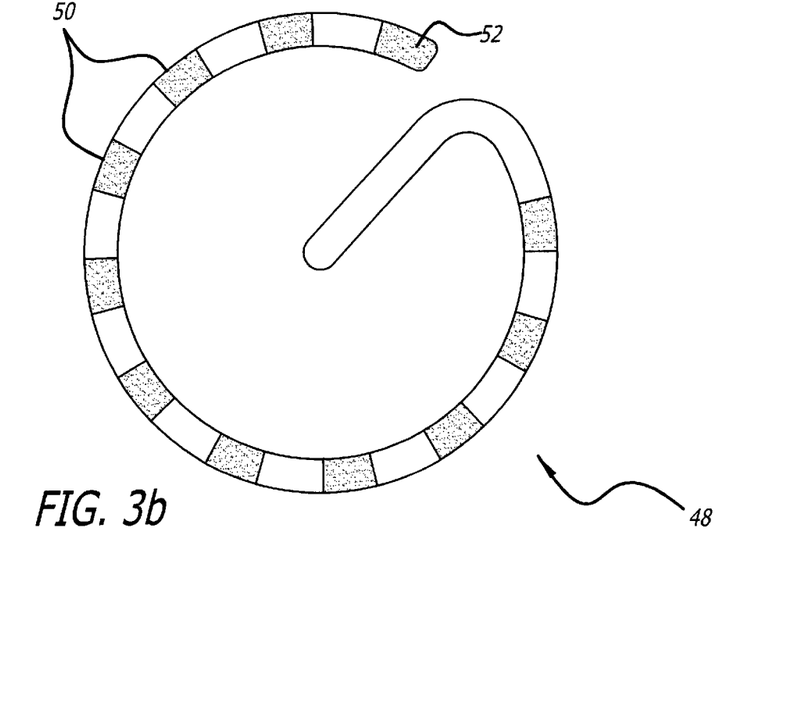
FIG. 3b is a diagram of another configuration of the electrode system of FIG. 2 having a tip electrode and several band electrodes arranged in a circular loop.
Figure 3C:
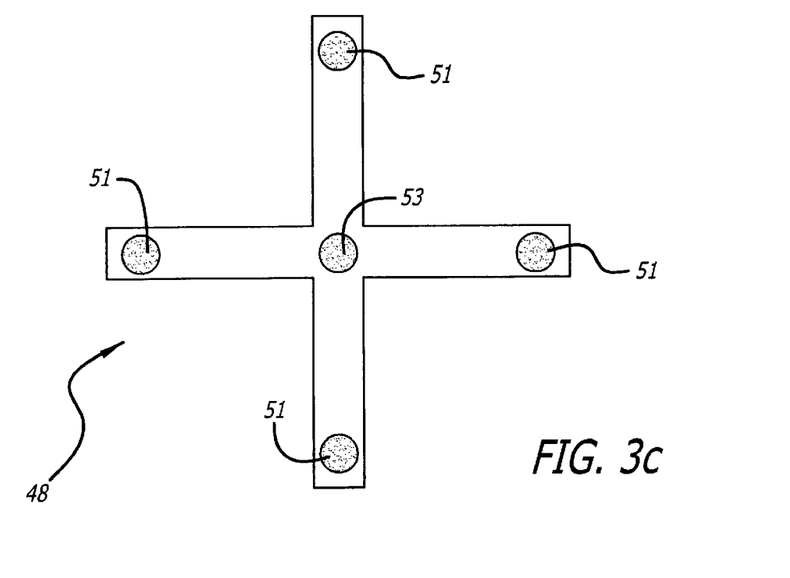
FIG. 3c is a diagram of another configuration of the electrode system of FIG. 2 having a central electrode and four orthogonally arranged branch electrodes.

The arrangement of the electrodes 50, 52 is not limited to a linear array and may take the form of other patterns. For example, as shown in FIG. 3b, the tip electrode 52 and the band electrodes 50 may be arranged in a circular loop. Alternatively, as shown in FIG. 3c, the electrode system 48 may include several branch electrodes 51 orthogonally arranged around a central electrode 53. A substantially linear array is preferred for certain therapeutic procedures, such as treatment of atrial fibrillation, in which linear lesions of typically 4 to 8 cm in length are desired. A linear array is more easily carried by the catheter sheath 20 and also lessens the size of the catheter.

The band electrodes 50 are formed of a material having a significantly higher thermal conductivity than that of the biological tissue to be ablated. Possible materials include silver, gold, chromium, aluminum, molybdenum, tungsten, nickel, platinum, and platinum/10% iridium. Because of the difference in thermal conductivity between the band electrodes 50 and the tissue, the electrodes cool off more rapidly in the flowing fluids at the biological site. The band electrodes 50 are sized so that the surface area available for contact with fluid in the heart, e.g., blood, is sufficient to allow for efficient heat dissipation from the electrodes to the surrounding blood. In a preferred embodiment, the band electrodes 50 are 7 French (2.3 mm in diameter) with a length of 3 mm.

Figure 4:
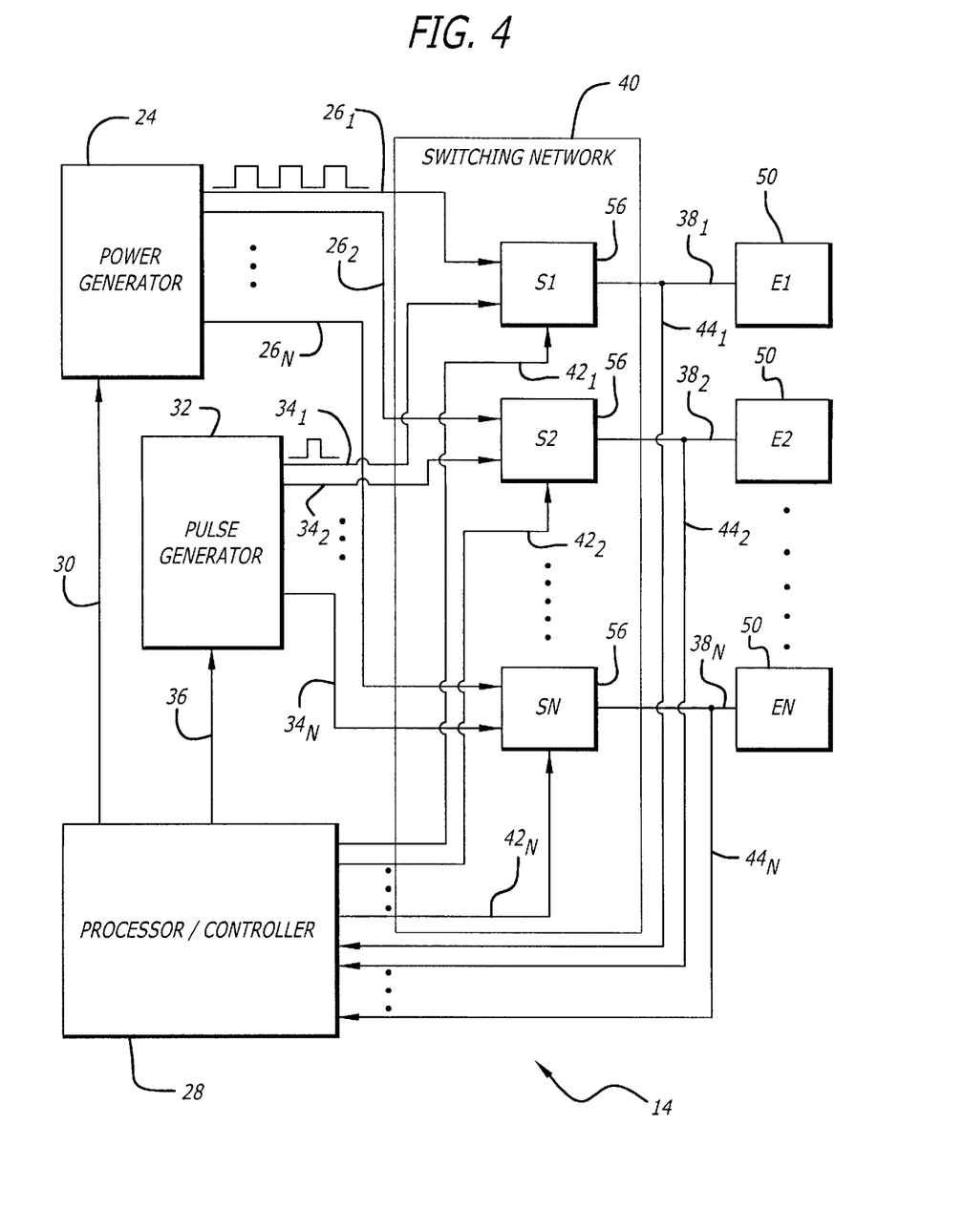
FIG. 4 is a detailed block diagram of the power control system of FIG. 1.

Referring now to FIG. 4, a block diagram of a multi-channel power control system 14 for use with a catheter system having a plurality of ablation electrodes 50 is shown. Although only three complete channels are shown, the system comprises many more as indicated by the successive dots. Those channels are not shown in FIG. 4 to preserve clarity of illustration. The power generator 24 is configured to provide a power output signal 26 to the electrodes in a manner that allows for both unipolar and bipolar application of energy through the biological tissue. To this end, the power generator 24 includes a plurality of output channels each of which produces its own power output signal 26 ($26_1$, $26_2$ through $26_N$ where "n" is the total number of channels). Typically the output signal 26 is a 500 kHz sine wave. Each power output signal 26 has alternating instances of peak power, i.e., "on" periods, and very low power, i.e., "off" periods. The power output signal 26 also has a variable duty cycle for controlling the length of the on periods and off periods. The duty cycle is controlled by power control signals 30 provided by the controller 28. The power output signals 26 also have controllable voltage levels and phases. Exemplary configurations of the power generator 24 and the controller 28 are described in U.S. Pat. Nos. 6,050,994, 6,059,778 and 6,171,305, the disclosures of which are hereby incorporated by reference. In alternate configurations, the power generator 24 may be configured to provide continuous wave power output signals 26, as opposed to duty cycle based signals.

The pulse generator 32 includes a plurality of controllable pulse generating circuits each of which is adapted to produce an energy pulse 34 ($34_1$, $34_2$ through $34_N$ where "n" is the total number of channels). The characteristics of the energy pulse 34, e.g., the voltage, timing and width, are selected such that the pulse is not pro-arrthymic, i.e., it does not induce cardiac arrthymia. Typically the energy pulse 34 is a square wave having a duration of approximately 0.5 milliseconds and an amplitude of 5 volts. The energy pulse 34 may be a single pulse or a sequence of pulses separated by a period of time. Each of the pulse generator circuits operates under the control of pulse control signals 36 received from the controller 28. The pulse generator circuits may comprise any of several conventional designs known to those of ordinary skill in the electrical arts.

The switching network 40 includes a plurality of output channels each having an associated switch 56. Input to each switch 56 is an output line from the power generator 24 and an output line from the pulse generator 32. Either of the power 26 from the power generator 24 or energy pulse 34 from the pulse generator 32 may be output over the lead line 38 to the electrode 50 associated with a particular switch 56. Operation of the switches 56 is controlled by switch control signals 42 received from the controller 28.

Figure 5A:
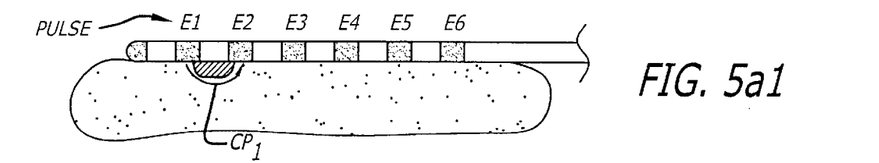
FIG. 5a depicts the distal segment of the catheter of FIG. 2 positioned against biological tissue, top and side views of a lesion resulting from a first ablation time period and the conduction path ($CP_1$) of a pulse originating at electrode E1 and terminating at electrode E2.
FIGS. 5b–5d depict the growth of the lesion of FIG. 5a resulting from subsequent second, third and fourth ablation time periods and the corresponding increase in the length of the conduction path of a pulse originating at electrode E1 and terminating at electrode E2.
Figure 5A:
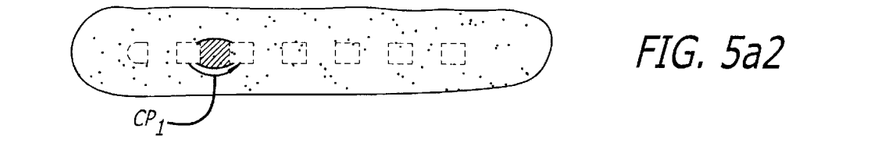
Figure 5B:
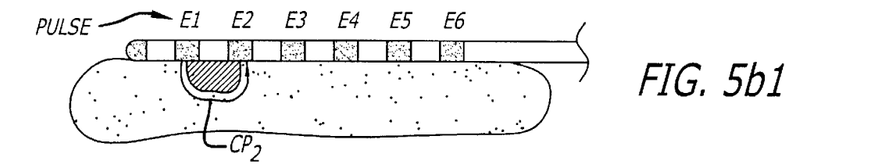
Figure 5B:
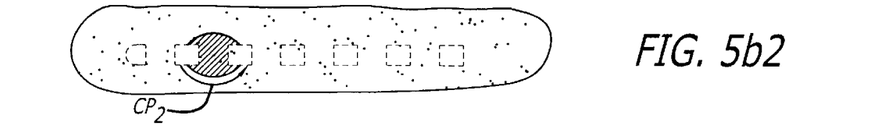
Figure 5C:
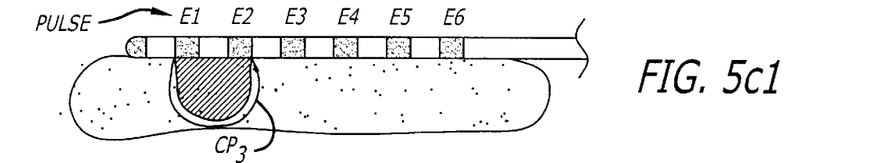
Figure 5C:
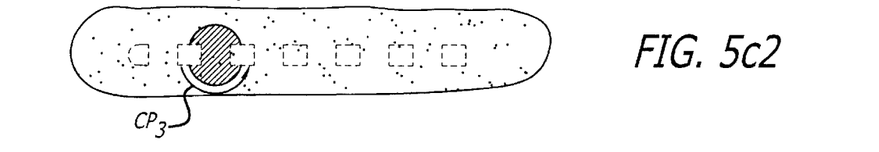
Figure 5D:
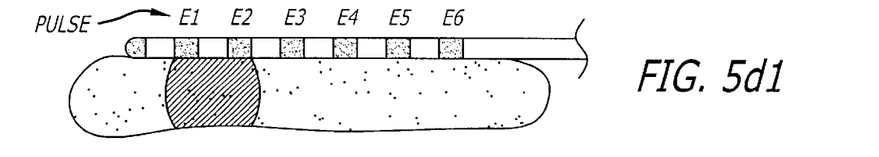
Figure 5D:
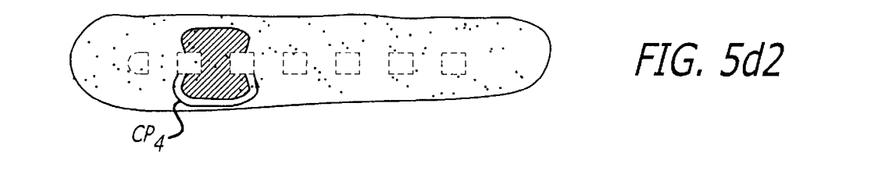

With reference to FIG. 5a, in operation, the electrode system 48 is positioned proximal to the biological tissue 12 such that at least two electrodes contact the tissue. In order to form a lesion between electrodes E1 and E2, the power control system 14 operates in an ablation mode. During the ablation mode, controller 28 (FIG. 4) controls the power generator 24 such that power $26_1$, $26_2$ is output to respective switches S1, S2. The controller 28 also outputs switch control signals $42_1$, $42_2$ to respective switches S1, S2 that cause the switches to output the power $26_1$, $26_2$ over lead lines $38_1$, $38_2$ to their associated electrode E1, E2. The power $26_1$, $26_2$ is applied to the tissue 12 (FIG. 5a) through electrodes E1 and E2 for a period of time, further referred to herein as an "ablation time period." The characteristics, e.g., phase, duty cycle, amplitude, etc., of the power $26_1$, $26_2$ and the modes, e.g., unipolar, bipolar, in which they are applied to the tissue may be as described in U.S. Pat. Nos. 6,050,994, 6,059,778 and 6,171,305, the disclosures of which, as previously mentioned, are hereby incorporated by reference. Power $26_1$, $26_2$ is applied for a time sufficient to form a lesion between electrodes E1 and E2. Throughout the ablation time period, the controller 28 controls the pulse generator 32 such that no energy pulses 34 are output to switches S1 and S2.

During an initial time period subsequent to the ablation time period, the power control system 14 switches to a "lesion-assessment mode." In this mode, the controller 28 controls the pulse generator 32 such that an energy pulse $34_1$ is output to switch S1. The controller 28 also outputs a switch control signal $42_1$ that causes switch S1 to output the energy pulse $34_1$ over lead line $38_1$ to electrode E1. Throughout the initial time period, the controller 28 controls the power generator 24 such that no power 26 is output to switches S1 and S2.

The controller/processor 28 monitors the energy pulse $34_1$ over monitor line $44_1$ and records the time the energy pulse was applied to electrode E1. The controller/processor 28 also monitors electrical activity at electrode E2 over the monitor line $44_2$ for receipt of the energy pulse applied to electrode E1 and records the time the pulse was received. Using the application time of the energy pulse $34_1$ and the receipt time of the energy pulse at electrode E2, the processor 28 calculates the conduction time between electrodes E1 and E2. The conduction time is stored in the processor 28 and maybe displayed on the display 58 of the power control system, as a numerical value or in a graphical format such as shown in FIG. 6.

With reference to FIGS. 5b, 5c and 5d, after completion of the initial lesion-assessment time period, the power control system 14 may automatically return to the ablation mode and repeat the ablation procedure for additional time periods in order to increase the size of the lesion. After each additional ablation period, the system 14 switches to the lesion assessment mode, applies another energy pulse to the electrode E1 and repeats the conduction time procedure just described. As shown in FIGS. 5a–5c, as the ablation lesion becomes larger, the shortest conduction path for the electrical pulse to electrode E2 increases. The conduction paths $CP_1$ through $CP_3$, and hence the conduction times, increase due to depth-wise increases in the lesion as shown in the various side views, and surface-size increases in the lesion as shown in the various top views. As shown in the top view of FIG. 5d, when the lesion becomes transmural, the conduction path is along the surface of the tissue along the lesion border.

Figure 6:
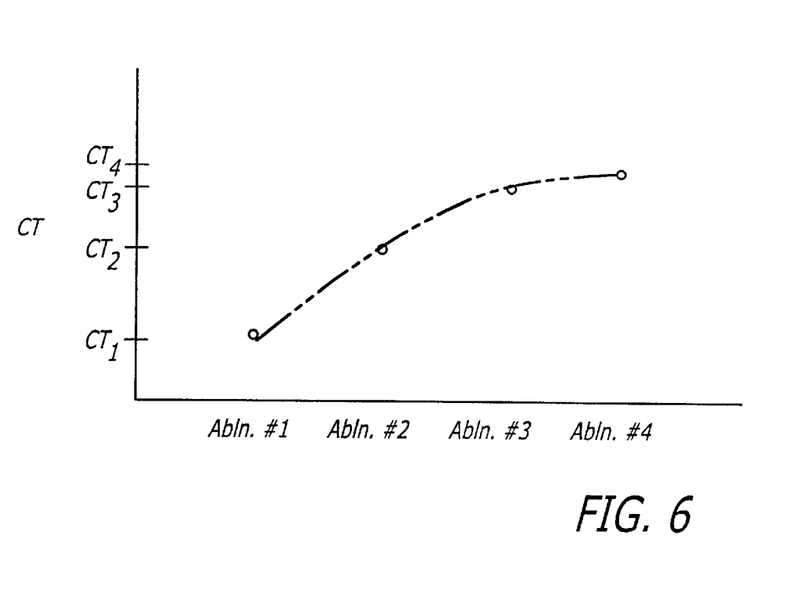
FIG. 6 is a graphical representation of the conduction time of the various conduction paths between electrode E1 and electrode E2 of FIGS. 5a–5d as a function of ablation time period.

With reference to FIG. 6, a plurality of conduction times may be plotted as a function of ablation time and the resulting graph reviewed to assess lesion efficacy. As a general rule, an increase in conduction time is indicative of a growing lesion. Over time, as a lesion becomes more transmural like the difference between conduction time measurements lessens and the graph flattens out.

In one embodiment of the invention, the processor monitors consecutive conduction times and calculates the difference between the times. The difference is compared to a preset value to determine lesion efficacy. In a preferred embodiment, the processor is programmed to determine the percentage difference between two consecutive conduction times and the preset value is a percentage value programmed into the processor. The preset value is manually set by the user through a processor interface, e.g., keyboard or front panel button, usually prior to system operation, but may be adjusted during operation. In one exemplary embodiment, the preset value is set between approximately 5% and 10% and when the percentage difference between consecutive conduction time is less than the preset value the processor provides an indication of an adequate lesion. In an alternate embodiment, the processor displays a graphical representation of a series of conduction times over a period of time, such as that shown in FIG. 6. The system user views the display and using his own judgment determines if the pattern of the conduction times are indicative of an adequate lesion. When the percentage difference between consecutive conduction times is at least as great as the preset value the processor may return to the ablation mode and apply more ablation energy to improve the efficacy of the lesion.

Figure 7A:
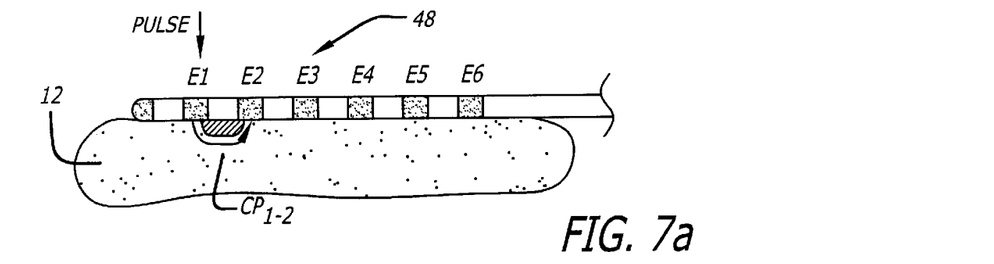
FIGS. 7a and 7b depicts the distal segment of the catheter of FIG. 2 positioned against biological tissue, the side view of a lesion resulting from a first ablation time period and the conduction path ($CP_{1\text{-}2}$) of a pulse originating at electrode E1 and terminating at electrode E2 (FIG. 7a) and the conduction path ($CP_{2\text{-}1}$) of a pulse originating at electrode E2 and terminating at electrode E1 (FIG. 7b)
Figure 7B:
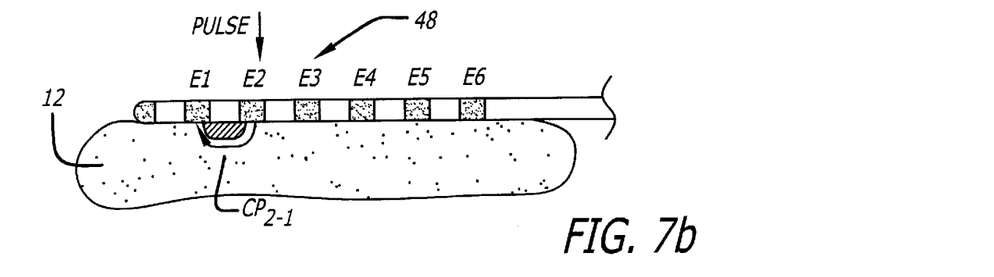

With reference to FIG. 7, in an alternate embodiment, the processor 28 is programmed to control the pulse generator 32 and switch S1 such that an energy pulse $34_1$ is applied to electrode E1. The conduction time for the pulse to propagate from electrode E1 to electrode E2 is measured and recorded by the processor. The controller 28 is also programmed to, during the same lesion-assessment time period, control the pulse generator 32 and switch S2 such that an energy pulse $34_2$ is applied to electrode E2 and to measure and record the conduction time for the pulse to propagate from electrode E2 to electrode E1. The processor then averages these two conduction time measurements to obtain an effective conduction time. Subsequent effective conduction time measurements are measured between subsequent ablation time periods to assess lesion efficacy.

Figure 8A:
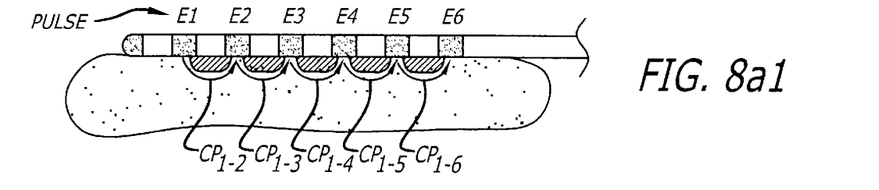
FIG. 8a depicts the distal segment of the catheter of FIG. 2 positioned against biological tissue, top and side views of a linear lesion resulting from a first ablation time period and the various conduction paths ($CP_{1\text{-}2}$–$CP_{1\text{-}6}$) of a pulse originating at electrode E1 and terminating at each of electrodes E2–E6.
FIGS. 8b and 8c depict the growth of the linear lesion of FIG. 8a resulting from subsequent second and third ablation time periods and the corresponding increase in the length of the conduction path of a pulse originating at electrode E1 and terminating at each of electrodes E2–E6.
Figure 8A:
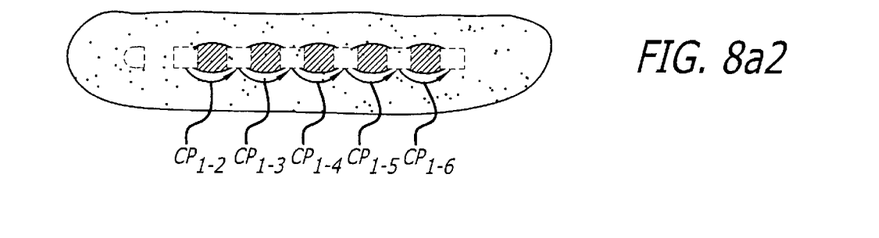
Figure 8B:
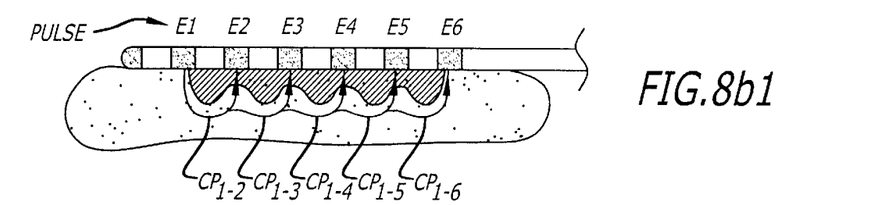
Figure 8B:
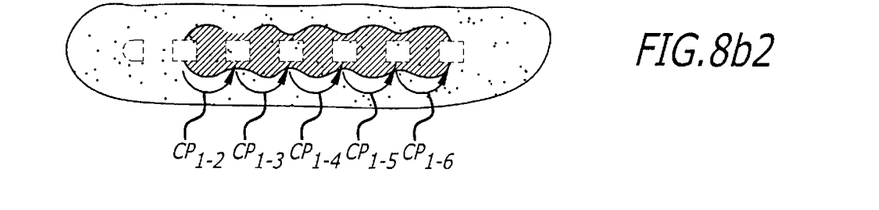
Figure 8C:
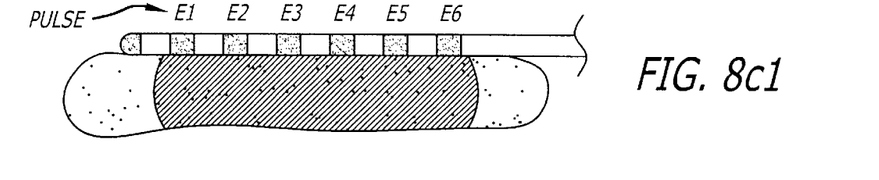
Figure 8C:
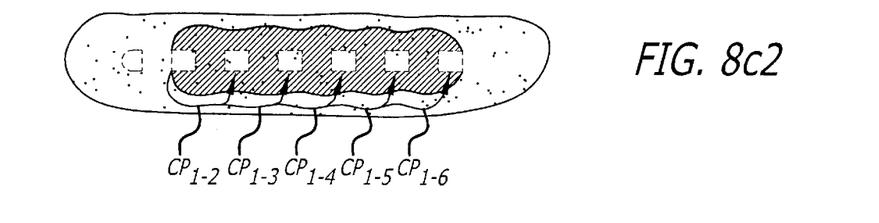

Conduction time measurements between one pulsed electrode and a plurality of other electrodes may be taken simultaneously in order to assess the efficacy of the linear lesion at various points along its length. With reference to FIGS. 8a–8c, an energy pulse $34_1$ is applied to electrode E1 and the electrical activity at each of remaining electrodes E2–E6 is monitored for receipt of the pulse to determine conduction times along the conduction paths $CP_{1-2}$ through $CP_{1-6}$. The process is repeated several times between ablation time periods. In this embodiment, the lesion-assessment time period must be long enough to allow sufficient time for the pulse to travel from E1 to E6. Applying the energy pulse 34 to one of the centrally located electrodes, such as E3, shortens the distance between the pulsed electrode and its most distant electrode E6 and thus reduces the lesion-assessment time period.

Figure 9:
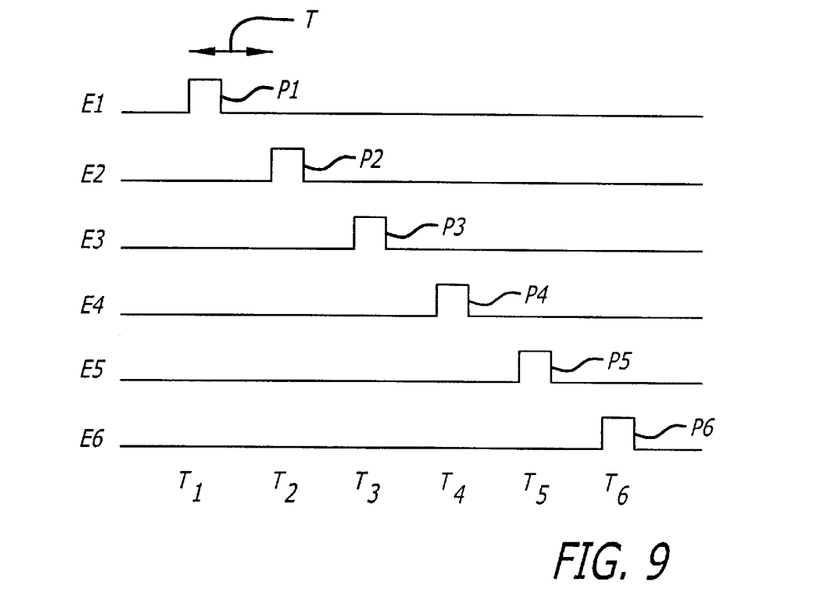
FIG. 9 is a plot of a series of pulses, each applied to one of six electrodes E1–E6 at a time $T_1$–$T_6$.
Figure 10A:
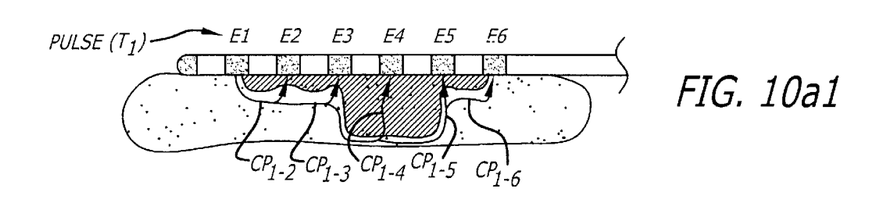
FIGS. 10a–10f depict the distal segment of the catheter of FIG. 2 positioned against biological tissue, top and side views of a linear lesion and the various conduction paths (CP) of pulses P1–P6 of FIG. 9.
Figure 10A:
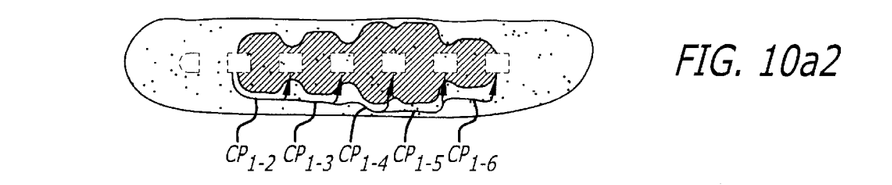
Figure 10B:
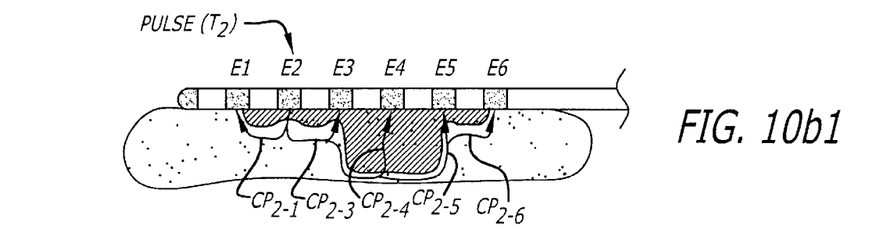
Figure 10B:
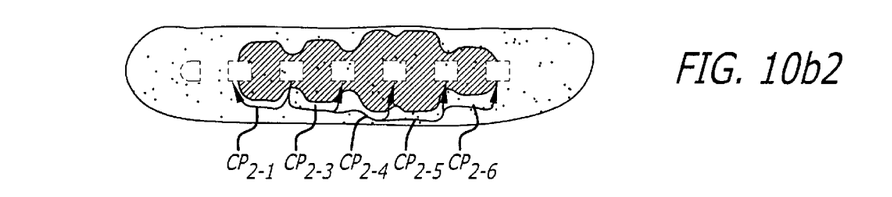
Figure 10C:
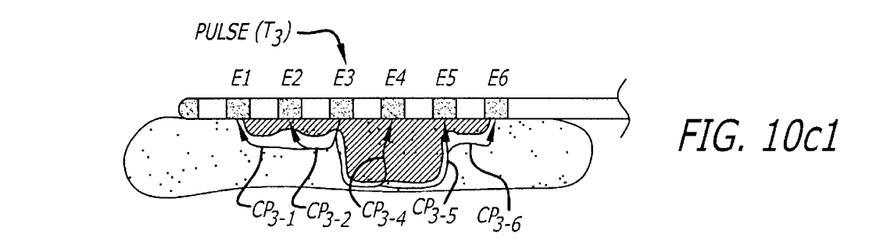
Figure 10C:
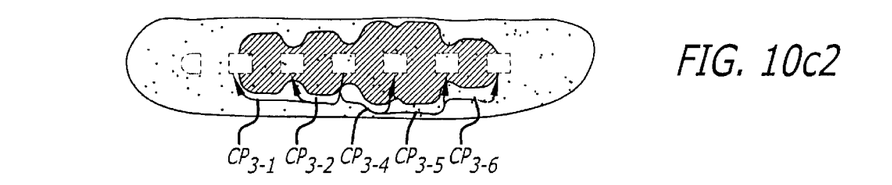
Figure 10D:
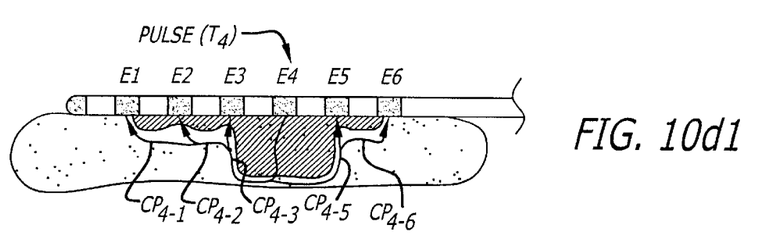
Figure 10D:
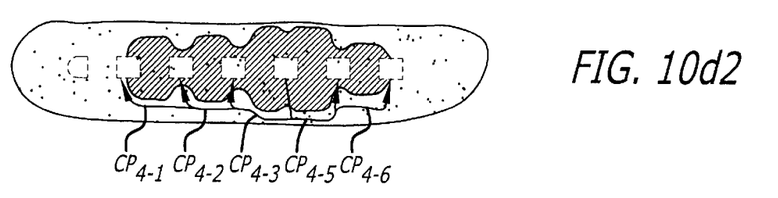
Figure 10E:
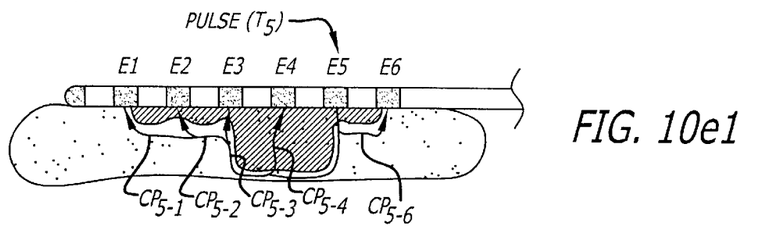
Figure 10E:
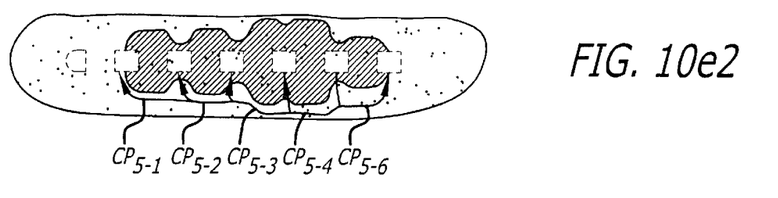
Figure 10F:
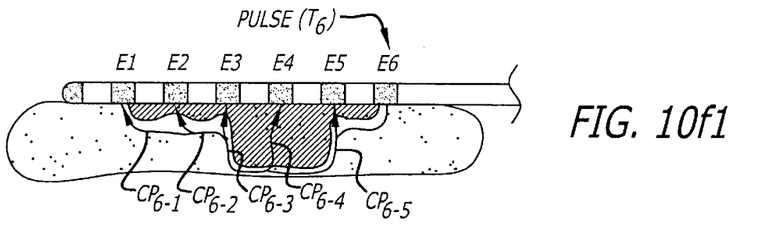
Figure 10F:
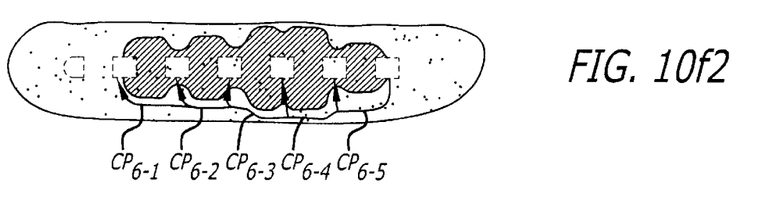

With reference to FIG. 9, in another configuration, the processor/controller 28 is programmed to control the pulse generator 24 to output a series of energy pulses P1–P6 between adjacent ablation time periods. One energy pulse is applied to one of the electrodes E1–E6 through its respective switch S1–S6. More specifically, pulse P1 is applied to electrode E1, pulse P2 is applied to electrode E2 and so on. The time T between consecutive pulses is long enough to allow the pulse to propagate through the tissue to the electrode most distant from the pulsed electrode. For example, the time between pulse P1 and pulse P2 is at least as great as the time it takes for pulse P1 to travel from electrode E1 to electrode E6, while the time between pulse P4 and pulse P5 is at least as great as the time it takes for pulse P4 to travel from electrode E4 to electrode E1. The separation time between each pulse may be the same for each pulse pair, i.e., the time between pulse P1 and P2 is the same as the time between pulses P2 and P3, P3 and P4, P4 and P5 and P5 and P6. In this case the separation time is the largest time required out of all of the electrode pairs, i.e., the time between electrode E1 and electrode E6. Alternatively the separation time may be different for each electrode pair.

As shown in FIGS. 10a–10f, the conduction times between the pulsed electrode and each of the remaining electrodes are collected for each pulse in the series. This process is repeated between several ablation time periods to collect sufficient time data to provide a meaningful lesion assessment. Prior to data analysis, the processor 28 may further process the data. For example, the processor may average complimentary conduction times, e.g., $CT_{1-3}$ and $CT_{3-1}$, $CT_{4-5}$ and $CT_{5-4}$, etc. Using the conduction time data, the processor 28 assesses the lesion along its length and identifies areas of the lesion requiring further ablation. For example, assuming FIGS. 10a–10f are indicative of a lesion after several periods of ablation, the data would indicate that the region of the lesion between electrodes E1 and E2, electrodes E2 and E3 and electrodes E5 and E6 require further ablation, while the region of the lesion between electrodes E3 and E4 and electrodes E4 and E5 is sufficiently ablated.

As previously mentioned, the power 26 used during the ablation mode may comprise alternating on and off periods and a duty cycle defining the durations of these periods. In one configuration of the invention, the controller 28 is programmed to measure conduction times during the off portions of the duty cycle. As such, ablation occurs during each on period of the duty cycle while a conduction time measurement is taken during an off period of the duty cycle. In a preferred embodiment, consecutive conduction time measurements are taken during consecutive off periods. In this configuration, the off period of the duty cycle is set by the controller 28 such that there is sufficient time for the pulse to travel from the pulsed electrode to the electrode most distant from the pulsed electrode.

Figure 11:
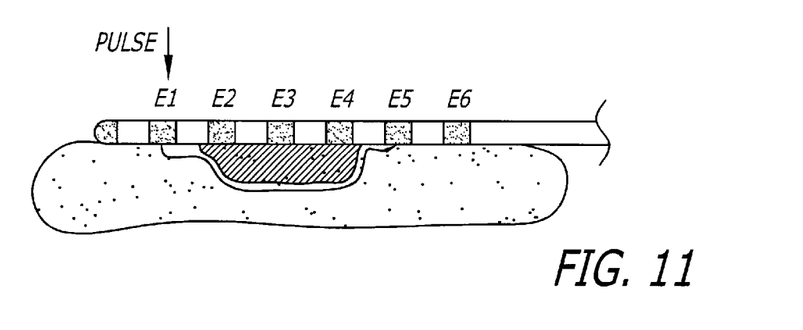
FIG. 11 depicts the distal segment of the catheter of FIG. 2 positioned against biological tissue, a lesion between electrodes E2 and E4 and the conduction path between electrodes E1 and E4.

In some ablation procedures the tissue immediately beneath an ablation electrode 50 may form a complete conduction block around the electrode. An energy pulse applied to the electrode 50 for purposes of lesion assessment may be blocked at the electrode thus hindering effective lesion assessment. To account for this possibility one or more of the electrodes 50, 52 may be used exclusively for lesion assessment and not for ablation during a given procedure. For example, with reference to FIG. 11, in order to determine the quality of the lesion between electrodes E2 and E4, the conduction times between the band electrode E1 immediately distal the most distal ablation electrode E2 and the band electrode E5 immediately proximal the most proximal ablation electrode E4 are measured in any of the manners previously described. As such, the possibility of the lesion-assessment energy pulse from the band electrode being blocked by the lesion is substantially eliminated.

The choice of which electrodes 50, 52 to use exclusively for lesion assessment may be made on a case by case basis by the user or may be automatically selected by the processor/controller 28. Prior to a procedure, the user may select which electrodes 50, 52 to use for ablation and which to use for lesion assessment. For example, with continued reference to FIG. 11, in order to form the lesion shown, the user would select electrodes E2 through E4 as ablation electrodes. The user would further select electrodes E1 and E5, positioned at opposite ends of the ablation electrodes, as lesion assessment electrodes. Alternatively, the processor/controller 28 may be programmed to automatically select the lesion assessment electrodes as the electrode immediately adjacent the most proximal and most distal ablation electrodes. In the situation where the most distal band electrode is functioning as an ablation electrode, the tip electrode 52 may be used as a lesion assessment electrode.

While the preceding description of the invention has focused on catheters with electrodes arranged in linear arrays, the invention is in no way limited to such configurations. With reference to FIGS. 3b and 3c, the electrode system 48 maybe configured in nonlinear arrays and for example, may be arranged in a circular array (FIG. 3b) or in a orthogonal array (FIG. 3c). Lesions formed by such arrangements may be linear like, e.g., a circular band for the loop arrangement of FIG. 3b, a cross for the orthogonal arrangement of FIG. 3c, or they may comprises an ablation area, e.g., a solid circle for the loop arrangement, a diamond shape for the orthogonal arrangement. In such arrangements the conduction times may be measured between adjacent electrodes or across the ablation area between opposite electrodes.

With reference to FIG. 3b, for a solid ablation circle having a boundary defined by the circular electrode arrangement, lesion efficacy may be assessed by measuring the conduction time across the ablation circle between electrodes 50 on opposite sides of the circle. For a circular ablation band, lesion efficacy may be assessed by measuring conduction time between adjacent electrodes 50. With reference to FIG. 3c, for a solid ablation diamond having a boundary defined by the branch electrodes 51, lesion efficacy may be assessed by measuring the conduction time across the ablation area between adjacent branch electrodes 51. For a cross shaped lesion efficacy may be assessed by measuring conduction time between the central electrode 53 and the branch electrodes 51.

Figure 12:
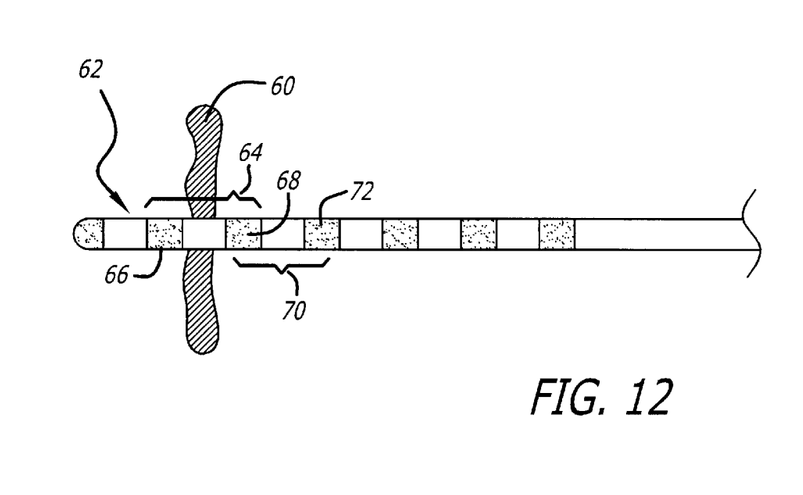
FIG. 12 depicts the distal segment of the catheter of FIG. 2 positioned against biological tissue in a cross-wise orientation relative to linear lesion.

With reference to FIG. 12, the catheter system of the invention may be further used to assess the efficacy of a lesion 60 by positioning the catheter 62 so that a first pair 64 of electrodes is positioned such that one electrode 66 is on one side of the lesion while the other electrode 68 is on the other side of the lesion. A second pair 70 of electrodes is positioned such that nonablated tissue is positioned between the electrodes 68, 72. The electrodes 66, 68 forming the first pair 64 and the electrodes 68, 72 forming the second pair 70 are spaced substantially the same distance apart so as to normalize conduction time measurements as described below. In a preferred embodiment, the pairs 64, 70 of electrodes share a common electrode 68.

In operation, a pulse of energy is applied to one of the electrodes in the first pair 64 and the other electrode in the pair is monitored for receipt of the pulse. The conduction time it takes for the pulse to reach the other electrode is recorded by the processor. A pulse of energy is also applied to one of the electrodes in the second pair 70, the other electrode in the pair is monitored for receipt of the pulse and the conduction time between the second pair of electrodes is determined. The processor calculates the difference between the two conduction times and compares the difference to a preset value. Because the spacing between the electrodes is substantially the same, any difference between the conduction times may be attributed to the condition of the tissue between the electrodes. If the difference is below the present value, the processor provides an indication that the lesion 60 is adequate.

With continue reference to FIG. 12, in another embodiment, the catheter system may be used to detect complete conduction blocks. For example, it is often desirable to create a complete conduction block around the ostium of the pulmonary vein such that aberrant electrical signals may not pass from the pulmonary vein into the atrium. By positioning the catheter 62 such that two electrodes 66, 68 are on opposite sides of the lesion 60, applying a pulse to one of the electrodes and monitoring the other electrode for receipt of the pulse, the system is able to determine is the lesion 60 forms a complete conduction block.

Figure 13A:
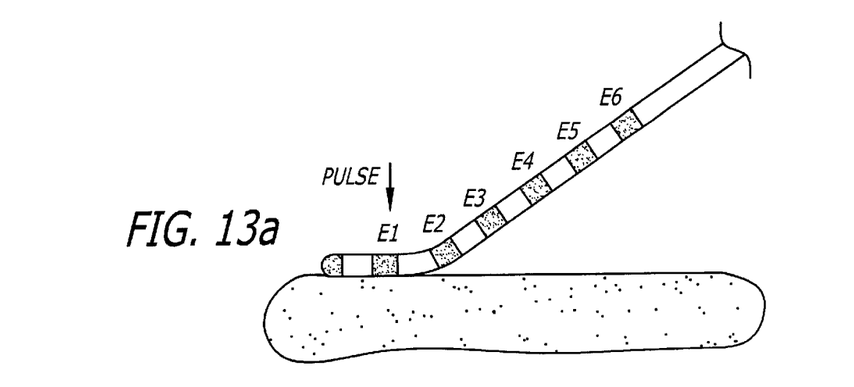
FIGS. 13a and 13b depict the distal segment of the catheter of FIG. 2 positioned against biological tissue such that several of the electrodes are not in contact with the tissue.

In another embodiment of the invention, energy pulses are used to provide an indication of electrode-tissue contact prior to ablation. With reference to FIG. 13a, to ensure that all electrodes necessary to perform a particular ablation procedure are in contact with the tissue, the catheter is positioned such that at least one of the electrodes is in contact with the tissue. A non pro-arrthymic pulse is applied to one of the electrodes known to be in contact with the tissue. Each of the remaining electrodes E2–E6 are monitored to determine if the pulse is sensed by the electrode. If the pulse is sensed by an electrode then it may be concluded that the electrode is positioned against the tissue. If the pulse is not sensed by an electrode, the catheter may be repositioned and the pulse applied again. This process may be repeated until each of the necessary electrodes senses a pulse.

Figure 13B:
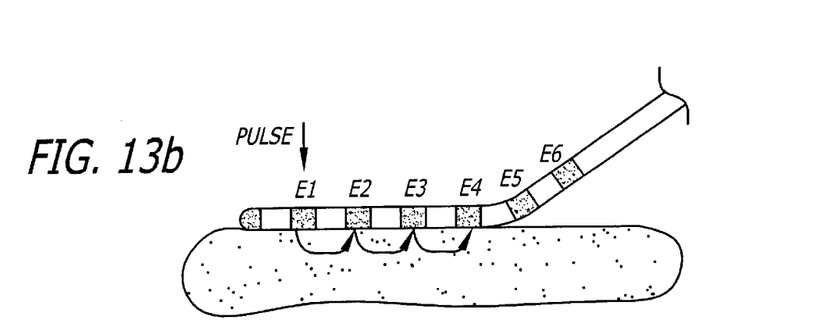

In FIG. 13a, electrode E1 is initially positioned against the tissue and a pulse is applied. The pulse is not sensed by any of electrodes E2–E6 because none of them are in contact with the tissue. In. FIG. 13b, the catheter is shown repositioned such that more of the electrodes contact the tissue. Upon application of another pulse to electrode E1, a pulse will be sensed at electrodes E2, E3 and E4 thereby confirming contact between these electrodes and the tissue. A similar process may be used any electrode system configuration, e.g., circular, orthogonal, etc.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. In an ablation procedure using a catheter system having a catheter with a plurality of electrodes and a generator system for providing ablation power and energy pulses to the electrodes, a method of assessing the efficacy of a biological tissue lesion between a pair of the electrodes, said method comprising:

a) during a first time period:
        applying a first pulse of energy to a first electrode;
        determining a first conduction time based on the time it takes for the pulse to conduct through the tissue to a second electrode;

b) during a time period subsequent to the first time period, applying ablation power to at least one of the first electrode and the second electrode;

c) during a time period subsequent to the application of ablation power:
        applying a subsequent pulse of energy to the first electrode;
        determining a subsequent conduction time based on the time it takes for the subsequent pulse to conduct through the tissue to the second electrode;

d) monitoring changes in the conduction times.

2. The method of claim 1 wherein monitoring changes in the conduction times comprises:
    calculating a difference between consecutive conduction times;
    comparing the difference to a preset value; and
    if the difference is below the preset value, providing an indication of an adequate lesion.

3. The method of claim 2 wherein the difference comprises the percentage change between consecutive conduction times and the preset value is between approximately 5% and 10%.

4. The method of claim 2 wherein the indication of an adequate lesion comprise a visual indication.

5. The method of claim 1 wherein monitoring changes in the conduction times comprises:
    calculating a difference between consecutive conduction times;
    comparing the difference to a preset value; and
    if the difference is at least as great as the preset value, applying ablation power to the electrodes to improve the efficacy of the lesion between the first electrode and a second electrode.

6. The method of claim 1 wherein monitoring changes in the conduction times comprises displaying a graph of the consecutive conduction times as a function of pulse-application time.

7. The method of claim 1 further comprising repeating steps c) and d) for a plurality of subsequent time periods.

8. The method of claim 1 wherein the second electrode comprises at least one of the plurality of electrodes other than the first electrode.

9. The method of claim 1 wherein the plurality of electrodes are arranged in a linear array, the first electrode comprises one of either the most proximal electrode or the most distal electrode and the second electrode comprises the other of the most proximal electrode and the most distal electrode.

10. The method of claim 1 wherein the plurality of electrodes are arranged in either one of a circular array and an orthogonal array, the first electrode comprises one of the electrodes and the second electrode comprises the electrode most diametrically opposite the first electrode.

11. The method of claim 1 wherein the plurality of electrodes are arranged in either one of a linear array, a circular array and a orthogonal array, the first electrode comprises any one of the electrodes and the second electrode comprises an electrode immediately adjacent the first electrode.

12. A system for assessing the efficacy of a biological tissue lesion between a first electrode and a second electrode positioned proximal to the biological tissue, said system comprising:

a generator system adapted to output ablation power and pulses of energy; and a processor adapted to:
(a) control the generator such that an energy pulse is provided to the first electrode at a first pulse-application time;
(b) monitor electrical activity at the second electrode for an indication that the energy pulse has been sensed by the second electrode and record the time at which the pulse was sensed;
(c) determine a conduction time based on the difference between the pulse-application time and the pulse-sense time; and
(d) control the generator such that ablation power is applied to at least one of the first electrode and the second electrode;
(e) repeat (a), (b) and (c) at least once, at a time subsequent to the the application of ablation power; and
(f) monitor changes in the conduction times.

13. The system of claim 12 wherein to monitor changes in the conduction times the processor is adapted to:
calculate a difference between consecutive conduction times;
compare the difference o a preset value; and
provide an indication of an adequate lesion when the difference is less than the preset value.

14. The system of claim 13 wherein the difference comprises the percentage change between consecutive conduction times and the preset value is between approximately 5% and 10%.

15. The system of claim 13 wherein the processor comprises a display and the indication of an adequate lesion comprises a visual indication.

16. The system of claim 12 wherein to monitor changes in the conduction times the processor is adapted to:
calculate a difference between consecutive conduction times;
compare the difference to a preset value; and
if the difference is at least as great as the preset value, apply ablation power to the electrodes to improve the efficacy of the lesion between the first electrode and a second electrode.

17. The system of claim 12 wherein the processor comprises a display and the processor is adapted to provide a graph of the consecutive conduction times as a function of pulse-application time on the display.

18. A method of ablating biological tissue using a catheter system having a catheter with a plurality of electrodes and a generator system for providing ablation power and energy pulses to the electrodes, said method comprising:
a) positioning the plurality of electrodes proximal to the biological tissue;
b) during a first time period applying ablation power to the electrodes to form a lesion between a first electrode and a second electrode;
c) during an initial time period subsequent to the first time period:
applying an initial pulse of energy to the first electrode;
determining an initial conduction time based on the time it takes for the pulse to conduct through the tissue to the second electrode;
d) during a time period subsequent to the initial time period:
applying a subsequent pulse of energy to the first electrode;
determining a subsequent conduction time based on the time it takes for the subsequent pulse to conduct through the tissue to the second electrode; and
e) monitoring changes in the conduction times.

19. The method of claim 18 wherein the generator system provides power having a duty cycle with alternating on periods and off periods, the first time period occurs during an on period of the duty cycle, and the initial time and subsequent time occur during an off period of the duty cycle.

20. The method of claim 19 wherein the initial time period and subsequent time period occur during different off periods.

21. The method of claim 19 wherein the initial time period and subsequent time period occur during consecutive off periods.

22. The method of claim 18 wherein monitoring changes in the conduction times comprises:
calculating a difference between consecutive conduction times;
comparing the difference to a preset value; and
if the difference is below the preset value, providing an indication of an adequate lesion.

23. The method of claim 18 wherein monitoring changes in the conduction times comprises:
calculating a difference between consecutive conduction times;
comparing the difference to a preset value; and
if the difference is at least as great as the preset value, applying ablation power to the electrodes to improve the efficacy of the lesion between the first electrode and a second electrode.

24. The method of claim 23 wherein the difference comprises the percentage change between consecutive conduction times and the preset value is between approximately 5% and 10%.

25. The method of claim 18 further comprising repeating steps c) and d) for a plurality of subsequent time periods.

26. A system for ablating biological tissue comprising:
a catheter having a plurality of electrodes adapted to be positioned proximal to the biological tissue;
a power generator adapted to output power having a duty cycle with alternating on periods and off periods;
a pulse generator adapted to output energy pulses; and
a processor adapted to:
(a) during a first time period, control the power generator such that power is applied to the electrodes to form a lesion between a first electrode and a second electrode;
(b) control the pulse generator such that an energy pulse is provided to the first electrode during an initial time period subsequent to the first time period;
(c) monitor electrical activity at the second electrode for an indication that the energy pulse has been sensed by the second electrode and record the time at which the pulse was sensed;
(d) determine a conduction time based on the difference between the pulse-application time and the pulse-sense time;
(e) repeat (b), (c) and (d) at least once, during a time period subsequent to the initial time period;
(f) monitor changes in the conduction times.

27. The system of claim 26 wherein the processor controls the power generator such that the first time period occurs during an on period of the duty cycle, and the initial time and subsequent time occur during an off period of the duty cycle.

28. The system of claim 27 wherein the initial time and subsequent time occur during different off periods.

29. The system of claim 27 wherein the initial time and subsequent time occur during consecutive off periods.

30. The system of claim 26 wherein to monitor changes in the conduction times the processor is adapted to:
- calculate a difference between consecutive conduction times;
- compare the difference to a preset value; and
- if the difference is above the preset value, control the power generator such that power is applied to the electrodes to improve the efficacy of the lesion between the first electrode and a second electrode.

31. The system of claim 30 wherein the difference comprises the percentage change between consecutive conduction times and the preset value is between approximately 5% and 10%.

32. The system of claim 26 further comprising repeating steps c) and d) for a plurality of subsequent time periods.

* * * * *